United States Patent
Fujimoto et al.

(10) Patent No.: US 10,941,376 B2
(45) Date of Patent: Mar. 9, 2021

(54) METHOD FOR PRODUCING CHIP FOR CELL CULTURE

(71) Applicants: TOKYO OHKA KOGYO CO., LTD., Kawasaki (JP); NATIONAL INSTITUTE OF ADVANCED INDUSTRIAL SCIENCE AND TECHNOLOGY, Tokyo (JP)

(72) Inventors: Takashi Fujimoto, Kawasaki (JP); Hidenori Miyamoto, Kawasaki (JP); Shinji Sugiura, Tsukuba (JP); Kazumi Shin, Tsukuba (JP); Fumiki Yanagawa, Tsukuba (JP); Toshiyuki Kanamori, Tsukuba (JP)

(73) Assignees: Tokyo Ohka Kogyo Co., Ltd., Kawasaki (JP); National institute of Advanced Industrial Science and Technology, Tokyo (JP)

( * ) Notice: Subject to any disclaimer, the term of this patent is extended or adjusted under 35 U.S.C. 154(b) by 238 days.

(21) Appl. No.: 15/824,081

(22) Filed: Nov. 28, 2017

(65) Prior Publication Data
US 2018/0179481 A1   Jun. 28, 2018

(30) Foreign Application Priority Data

Dec. 27, 2016   (JP) .............................. JP2016-253304

(51) Int. Cl.
*C12M 3/06* (2006.01)
*B01J 19/00* (2006.01)
(Continued)

(52) U.S. Cl.
CPC .......... *C12M 23/16* (2013.01); *B01J 19/0046* (2013.01); *B01J 19/0093* (2013.01);
(Continued)

(58) Field of Classification Search
CPC .. C12M 23/16; B01J 19/0046; B01J 19/0093; C09J 167/02; G01N 35/00029
See application file for complete search history.

(56) References Cited

U.S. PATENT DOCUMENTS 4,853,262 A * 8/1989 Horie ..................... C09J 133/06
428/13
6,752,966 B1 * 6/2004 Chazan ............. B01L 3/502707
422/500
(Continued)

FOREIGN PATENT DOCUMENTS

| JP | A-2005-208527 | 8/2005 |
| JP | A-2007-031602 | 2/2007 |

(Continued)

OTHER PUBLICATIONS

Search Report in European Patent Application No. 17209880.8, dated Jun. 7, 2018.
(Continued)

*Primary Examiner* — Daniel McNally
(74) *Attorney, Agent, or Firm* — Knobbe Martens Olson & Bear LLP (57) ABSTRACT

A method for producing a chip for cell culture that enables production of a microchannel structure, enables mass production at low cost, and also has functions suited to cell culture. The method includes forming a photosensitive adhesive layer by applying a photosensitive adhesive to a first substrate having transparency, thus obtaining a 3D printing substrate, 3D printing steps that employ vat photopolymerization, forming a first adhesive layer by depositing a first adhesive on a second substrate having transparency, thus obtaining a cell culture channel top plate, and bonding the cell culture channel and the cell culture channel top plate together via the first adhesive layer, and then performing thermocompression bonding to obtain a microchannel struc- (Continued)

tural body having a hollow structure, wherein the first adhesive is a polyester-based resin having a Tg value of 5° C. or higher.

4 Claims, 2 Drawing Sheets

(51) Int. Cl.
    *G01N 35/00*     (2006.01)
    *C09J 167/02*     (2006.01)
    *C12M 1/26*     (2006.01)
    *C12M 1/00*     (2006.01)
    *B33Y 10/00*     (2015.01)
    *C09J 4/06*     (2006.01)

(52) U.S. Cl.
    CPC ............. *B33Y 10/00* (2014.12); *C09J 167/02* (2013.01); *C12M 23/22* (2013.01); *C12M 33/00* (2013.01); *G01N 35/00029* (2013.01); *B01L 2300/0819* (2013.01); *C09J 4/06* (2013.01); *G01N 2035/00158* (2013.01)

(56) References Cited

U.S. PATENT DOCUMENTS

| | | |
|---|---|---|
| 2004/0253545 A1 | 12/2004 | David |
| 2005/0170498 A1 | 8/2005 | Dolley et al. |
| 2007/0037277 A1 | 2/2007 | Shuler et al. |
| 2011/0268948 A1 | 11/2011 | Ikuta et al. |
| 2012/0009665 A1* | 1/2012 | Lin .................. B01L 3/502707 435/287.2 |
| 2012/0129208 A1* | 5/2012 | Khine .................. B01L 3/5085 435/29 |
| 2013/0037207 A1* | 2/2013 | Yamamoto ........ B01L 3/502707 156/273.3 |
| 2014/0048980 A1* | 2/2014 | Crump .................. B33Y 10/00 264/401 |
| 2017/0137767 A1 | 5/2017 | Senzaki |

FOREIGN PATENT DOCUMENTS

| | | | |
|---|---|---|---|
| JP | A-2007-526767 | 9/2007 | |
| JP | A-2010-104285 | 5/2010 | |
| JP | A-2010-112730 | 5/2010 | |
| JP | A-2013-164311 | 8/2013 | |
| JP | A-2014-092328 | 5/2014 | |
| JP | A-2015-204768 | 11/2015 | |
| JP | A-2015-535728 | 12/2015 | |
| WO | WO 2009/042671 A1 | 4/2009 | |
| WO | WO-2009042671 A1 * | 4/2009 | ........ B01L 3/502707 |
| WO | WO 2014/046621 A1 | 3/2014 | |
| WO | WO 2014/197999 A1 | 12/2014 | |
| WO | WO 2016/164861 A1 | 10/2016 | |

OTHER PUBLICATIONS

Office Action in Japanese Patent Application No. 2016-253304, dated Aug. 11, 2020.

* cited by examiner

METHOD FOR PRODUCING CHIP FOR CELL CULTURE

TECHNICAL FIELD

The present invention relates to a method for producing a chip for cell culture.

BACKGROUND ART

In monolayer culture, which has typically been used for conventional cell assays, the environment that surrounds the cells differs significantly from an in vivo environment, and the fact that cultured cells can lose many of the functions that are expressed in vivo causes frequent problems. In recent years, advances in microfabrication technology and three-dimensional culture techniques have begun to address these problems, and are expected to yield improvements in both the throughput and the reliability of cell assays. In particular, the concept of an organ-on-a-chip, wherein a cell culture chip having a microfluidic device that replicates, in vitro, a physiological three-dimensional culture environment is treated as a single organ, is becoming more widespread, and much research is being conducted worldwide into potential applications of such chips to drug development. Moreover, the concept of a body-on-a-chip, in which a plurality of organ models each reconstructed in vitro are connected by microchannels or the like with the aim of replicating individual responses, has also been advocated, and is rapidly attracting attention.

The types of chips for cell culture described above are produced by soft lithography methods (for example, see Patent Document 1) or by injection molding methods (for example, see Patent Document 2).

PRIOR ART LITERATURE

Patent Documents

Patent Document 1: Japanese Translation of PCT International Application, Publication No. 2015-535728
Patent Document 2: Japanese Unexamined Patent Application, First Publication No. 2010-112730

DISCLOSURE OF INVENTION

Problems to be Solved by the Invention

Among conventional methods for producing chips for cell culture, the soft lithography method enables the production of microchannel structures, but is only suitable for small-scale production, and has proven unsuitable for mass production. In contrast, the injection molding method is suitable for mass production, but requires the production of a mold with microchannel structures, and is therefore costly.

Further, in chips for cell culture, it is desirable that in addition to enabling cell culture, the chip also has other functions such as the ability to observe the interior of the chip.

The present invention has been developed in light of these circumstances, and provides a method for producing a chip for cell culture that enables production of a microchannel structure, enables mass production at low cost, and also has functions suited to cell culture.

Means for Solving the Problems

A first aspect of the present invention is a method for producing a chip for cell culture, the method having a step A of forming a photosensitive adhesive layer by applying a photosensitive adhesive to a first substrate having transparency, thus obtaining a 3D printing substrate, a step B of depositing a photosensitive molding material on the 3D printing substrate to form a photosensitive molding material layer, and then selectively irradiating the photosensitive molding material layer with ultraviolet rays to selectively cure the photosensitive molding material layer, a step C of overlaying another photosensitive molding material layer by depositing a photosensitive molding material on the selectively cured photosensitive molding material layer, and then selectively irradiating the overlaid photosensitive molding material layer with ultraviolet rays to selectively cure the overlaid photosensitive molding material layer, a step D of repeating the step C a plurality of times, and subsequently developing the uncured portions to obtain a cell culture channel, a step E of forming a first adhesive layer by depositing a first adhesive on a second substrate having transparency, thus obtaining a cell culture channel top plate, and a step F of bonding the cell culture channel and the cell culture channel top plate together via the first adhesive layer, and then performing thermocompression bonding to obtain a microchannel structural body having a hollow structure, wherein the first adhesive is a polyester-based resin having a Tg value of 5° C. or higher.

Effects of the Invention

The present invention can provide a method for producing a chip for cell culture that can produce a microchannel structure and enables mass production at low cost.

EMBODIMENTS FOR CARRYING OUT THE INVENTION

<<Method for Producing Chip for Cell Culture>>

First Embodiment

One embodiment of the present invention provides a method for producing a chip for cell culture, the method having a step A of forming a photosensitive adhesive layer by applying a photosensitive adhesive to a first substrate having transparency, thus obtaining a 3D printing substrate, a step B of depositing a photosensitive molding material on the 3D printing substrate to form a photosensitive molding material layer, and then selectively irradiating the photosensitive molding material layer with ultraviolet rays to selectively cure the photosensitive molding material layer, a step C of overlaying another photosensitive molding material layer by depositing a photosensitive molding material on the selectively cured photosensitive molding material layer, and then selectively irradiating the overlaid photosensitive molding material layer with ultraviolet rays to selectively cure the overlaid photosensitive molding material layer, a step D of repeating the step C a plurality of times, and subsequently developing the uncured portions to obtain a cell culture channel, a step E of forming a first adhesive layer by depositing a first adhesive on a second substrate having transparency, thus obtaining a cell culture channel top plate, and a step F of bonding the cell culture channel and the cell culture channel top plate together via the first adhesive layer, and then performing thermocompression bonding to obtain a microchannel structural body having a hollow structure, wherein the first adhesive is a polyester-based resin having a Tg value of 5° C. or higher.

The method for producing a chip for cell culture according to this embodiment enables a cell culture chip having a microchannel structure to be mass-produced at low cost.

Figure 1:
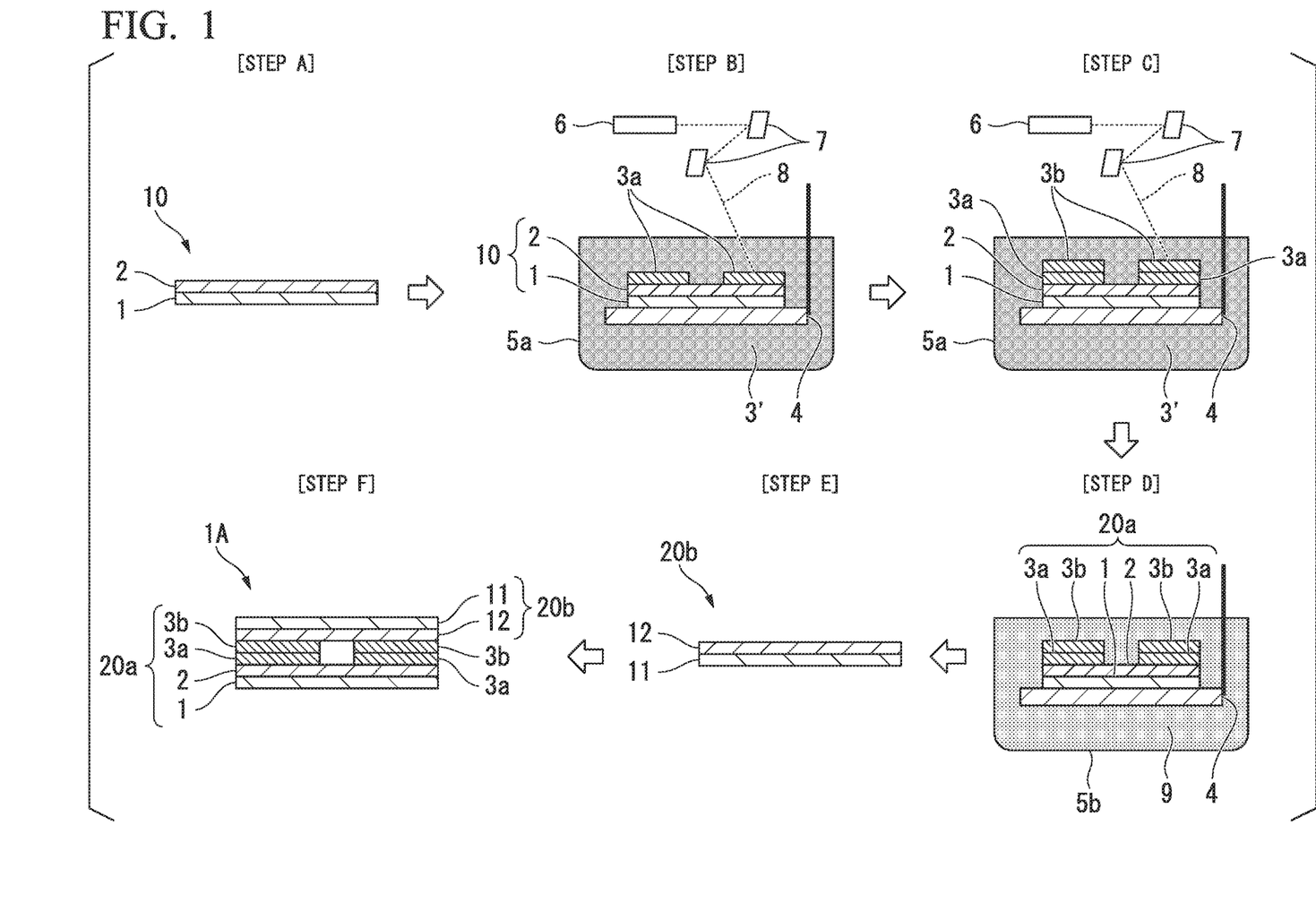
FIG. 1 is a series of cross-sectional views schematically illustrating the composition of each step in order to describe one embodiment of the method for producing a chip for cell culture according to the present invention.

The chip for cell culture of the present embodiment is described below in detail with reference to the drawings. FIG. 1 is a series of cross-sectional views schematically illustrating the composition of each step in order to describe one embodiment of the method for producing a chip for cell culture according to the present invention.

[Step A]

First, a photosensitive adhesive is applied to a first substrate 1 having transparency. By leaving the photosensitive adhesive to stand for a certain time to dry, a photosensitive adhesive layer 2 is formed, thus obtaining a 3D printing substrate (see [Step A] of FIG. 1).

(First Substrate)

From the viewpoint of enabling observation of the cultured cells using a phase contrast microscope or the like, the first substrate preferably has transparency. Further, in order to enhance the transparency, the substrate preferably contains no fillers (antiblocking agents).

The material for the first substrate is preferably a transparent low-autofluorescence material. Favorable examples of low-autofluorescence materials include glass, polyethylene terephthalates, polycarbonates, cycloolefin polymers, polydimethylsiloxanes, polystyrenes and polyacrylates (acrylic resins).

More specific examples of the polyacrylates (acrylic resins) include poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly(octadecyl acrylate).

The thickness of the first substrate may be at least 50 μm but not more than 250 μm, and for example is preferably at least 100 μm but not more than 230 μm, or at least 150 μm but not more than 200 μm.

The first substrate may have a slip layer containing a lubricant component on at least one surface.

There are no particular limitations on the lubricant component, and examples include paraffin wax, micro wax, polypropylene wax, polyethylene wax, ethylene-acrylic-based wax, stearic acid, behenic acid, 12-hydroxystearic acid, stearamide, oleamide, erucamide, methylenebisstearamide, ethylenebisstearamide, ethylenebisoleamide, butyl stearate, stearic acid monoglyceride, pentaerythritol tetrastearate, hydrogenated castor oil, stearyl stearate, siloxane, higher alcohol-based polymers, stearyl alcohol, calcium stearate, zinc stearate, magnesium stearate, lead stearate, silicone (dimethylsiloxane)-based low-molecular weight materials (oils) and silicone (dimethylsiloxane)-based resins, and these components may be used individually, or in combinations containing two or more components.

Further, examples of binder resin components that may be included in the slip layer include various resins such as polyester-based resins, polyamide-based resins, polyurethane-based resins, epoxy-based resins, phenol-based resins, acrylic-based resins, polyvinyl acetate-based resins, cellulose-based resins, styrene-based resins, or copolymers of these resins. Among these, in terms of achieving superior lubrication properties in combination with the lubricant described above, a styrene-acrylic-based copolymer resin is preferred as the binder resin component.

There are no particular limitations on the method used for forming the slip layer, and examples include a method in which the slip layer is formed by so-called inline coating, by coating the base substrate material prior to stretching during production of the first substrate, and then performing stretching, and a lamination method that uses coextrusion.

In this description, the term "silicone-based" describes organosiloxanes, which can exist in oil-like, rubber-like or resin-like forms known as silicone oils, silicone rubbers and silicone resins respectively. All of these silicone-based materials have a water repellency action, a lubrication action, and a release action and the like, and are effective at reducing surface friction upon inclusion in the film outermost layer.

The thickness of the slip layer is, for example, not more than 0.1 μm, and is preferably 50 nm or less.

(Photosensitive Adhesive)

The photosensitive adhesive preferably has developer resistance. By ensuring that the photosensitive adhesive has developer resistance, the photosensitive adhesive is not eluted in the subsequent developing treatment of step D, meaning good adhesion can be maintained. Further, the photosensitive adhesive preferably exhibits adhesiveness to the first substrate, adhesiveness to the cell culture channel formed in the subsequent steps B to D, good transparency, low autoluminescence, and low cytotoxicity.

Photopolymerizable Compound

The material of the photosensitive adhesive can be selected from among all manner of photopolymerizable compounds used in conventional photosensitive adhesives. In terms of the storage stability of the photosensitive adhesive, the photopolymerizable compound is preferably a compound having an ethylenic unsaturated bond. Examples of the photopolymerizable functional group contained in the compound having an ethylenic unsaturated bond include a (meth)acryloyl group, a vinyl group and an allyl group. Examples of compounds that can be used as the compound having an ethylenic unsaturated bond include monofunctional, difunctional, and trifunctional or higher (meth)acrylate compounds, (meth)acrylamide compounds, vinyl compounds and allyl compounds. These compounds having an ethylenic unsaturated bond may be used individually, or in combinations containing two or more compounds.

Examples of monofunctional compounds having an ethylenic unsaturated bond include (meth)acrylate esters, (meth)acrylamides, allyl compounds, vinyl ethers, vinyl esters, and styrenes.

Examples of the (meth)acrylate esters include methyl (meth)acrylate, ethyl (meth)acrylate, propyl (meth)acrylate, amyl (meth)acrylate, t-octyl (meth)acrylate, chloroethyl (meth)acrylate, 2,2-dimethylhydroxypropyl (meth)acrylate, 2-hydroxyethyl (meth)acrylate, trimethylolpropane mono (meth)acrylate, benzyl (meth)acrylate, furfuryl (meth)acrylate, phenyl (meth)acrylate, (meth)acrylates of EO adducts of phenol, (meth)acrylates of PO adducts of phenol, (meth)acrylates of EO/PO co-adducts of phenol, ethylene glycol mono(meth)acrylate, diethylene glycol mono(meth)acrylate, triethylene glycol mono(meth)acrylate, polyethylene glycol mono(meth)acrylate, 2-methoxyethyl (meth)acrylate, diethylene glycol monomethyl ether mono(meth)acrylate, triethylene glycol monomethyl ether mono(meth)acrylate, polyethylene glycol monoethyl ether mono(meth)acrylate, propylene glycol mono(meth)acrylate, dipropylene glycol mono(meth)acrylate, tripropylene glycol mono(meth)acrylate, polypropylene glycol mono(meth)acrylate, propylene glycol monomethyl ether mono(meth)acrylate, dipropylene glycol monomethyl ether mono(meth)acrylate, tripropylene glycol monomethyl ether mono(meth)acrylate, polypropylene glycol monomethyl ether mono(meth)acrylate, mono (meth)acrylates of EO/PO copolymers, monomethyl ether mono(meth)acrylates of EO/PO copolymers, and amine-modified polyether acrylates.

In this description, "EO-modified" means a compound having a (poly)oxyethylene chain, "PO-modified" means a compound having a (poly)oxypropylene chain, and "EO/PO-modified" means a compound having both a (poly)oxyethylene chain and a (poly)oxypropylene chain.

Examples of the (meth)acrylamides include (meth)acrylamide, N-alkyl(meth)acrylamides, N-aryl(meth)acrylamides, N,N-dialkyl(meth)acrylamides, N,N-diaryl(meth)acrylamides, N-methyl-N-phenyl(meth)acrylamide, and N-hydroxyethyl-N-methyl(meth)acrylamide.

Examples of the allyl compound include allyl esters such as allyl acetate, allyl caproate, allyl caprylate, allyl laurate, allyl palmitate, allyl stearate, allyl benzoate, allyl acetoacetate and allyl lactate; and allyloxyethanol.

Examples of the vinyl ethers include alkyl vinyl ethers such as hexyl vinyl ether, octyl vinyl ether, decyl vinyl ether, ethylhexyl vinyl ether, methoxyethyl vinyl ether, ethoxyethyl vinyl ether, chloroethyl vinyl ether, 1-methyl-2,2-dimethylpropyl vinyl ether, 2-ethylbutyl vinyl ether, hydroxyethyl vinyl ether, diethylene glycol vinyl ether, dimethylaminoethyl vinyl ether, diethylaminoethyl vinyl ether, butylaminoethyl vinyl ether, benzyl vinyl ether and tetrahydrofurfuryl vinyl ether; and vinyl aryl ethers such as vinyl phenyl ether, vinyl tolyl ether, vinyl chlorophenyl ether, vinyl 2,4-dichlorophenyl ether, vinyl naphthyl ether, and vinyl anthranyl ether.

Examples of the vinyl esters include vinyl butyrate, vinyl isobutyrate, vinyl trimethylacetate, vinyl diethylacetate, vinyl valerate, vinyl caproate, vinyl chloroacetate, vinyl dichloroacetate, vinyl methoxyacetate, vinyl butoxyacetate, vinyl phenylacetate, vinyl acetoacetate, vinyl lactate, vinyl-β-phenylbutyrate, vinyl benzoate, vinyl salicylate, vinyl chlorobenzoate, vinyl tetrachlorobenzoate, and vinyl naphthoate.

Examples of the styrenes include styrene; alkylstyrenes such as methylstyrene, dimethylstyrene, trimethylstyrene, ethylstyrene, diethylstyrene, isopropylstyrene, butylstyrene, hexylstyrene, cyclohexylstyrene, decylstyrene, benzylstyrene, chloromethylstyrene, trifluoromethylstyrene, ethoxymethylstyrene and acetoxymethylstyrene; alkoxystyrenes such as methoxystyrene, 4-methoxy-3-methylstyrene and dimethoxystyrene; and halostyrenes such as chlorostyrene, dichlorostyrene, trichlorostyrene, tetrachlorostyrene, pentachlorostyrene, bromostyrene, dibromostyrene, iodostyrene, fluorostyrene, trifluorostyrene, 2-bromo-4-trifluoromethylstyrene and 4-fluoro-3-trifluoromethylstyrene.

Examples of difunctional compounds having an ethylenic unsaturated bond include polyethylene glycol di(meth)acrylate, polypropylene glycol di(meth)acrylate, polyethylene polypropylene glycol di(meth)acrylate, ethylene glycol di(meth)acrylate, propylene glycol di(meth)acrylate, polyethylene polytrimethylolpropane di(meth)acrylate, 2-(meth)acryloyloxy-2-hydroxypropyl phthalate, 2-(meth)acryloyloxyethyl-2-hydroxyethyl phthalate, compounds obtained by reacting an α,β-unsaturated carboxylic acid with a glycidyl group-containing compound, urethane monomers, γ-chloro-β-hydroxypropyl-β'-(meth)acryloyloxyethyl-o-phthalate, β-hydroxyethyl-β'-(meth)acryloyloxyethyl-o-phthalate, β-hydroxypropyl-β'-(meth)acryloyloxyethyl-o-phthalate, and isocyanuric acid EO-modified diacrylate.

Examples of the compounds obtained by reacting an α,β-unsaturated carboxylic acid with a glycidyl group-containing compound include triglycerol di(meth)acrylate and the like. Examples of the aforementioned urethane monomers include addition reaction products of a (meth)acrylic monomer having a hydroxyl group at the β-position with isophorone diisocyanate, 2,6-toluene diisocyanate, 2,4-toluene diisocyanate or 1,6-hexamethylene diisocyanate or the like, EO-modified urethane di(meth)acrylates, and EO/PO-modified urethane di(meth)acrylates.

Examples of polyfunctional compounds having an ethylenic unsaturated bond include trifunctional or higher acrylates such as trimethylolpropane tri(meth)acrylate, pentaerythritol tetra(meth)acrylate, EO-modified pentaerythritol tetra(meth)acrylate, PO-modified pentaerythritol tetra(meth)acrylate, dipentaerythritol penta(meth)acrylate and dipentaerythritol hexa(meth)acrylate; polyfunctional urethane (meth)acrylates obtained by reacting a polyisocyanate compound and a hydroxy group-containing (meth)acrylate monomer (for example, isocyanuric acid EO-modified triacrylates); and condensed products of a polyhydric alcohol and N-methylol(meth)acrylamide.

Photopolymerization Initiator

The photosensitive adhesive contains a photopolymerization initiator in an amount of at least 0.5% by mass but not more than 5.0% by mass, and preferably at least 1.0% by mass but not more than 4.0% by mass, relative to the mass of the photosensitive adhesive. By including a photopolymerization initiator in this type of amount in the photosensitive adhesive, it is possible to reduce the cytotoxicity caused by residual monomers or photopolymerization initiator within the photosensitive adhesive layer obtained upon curing the photosensitive adhesive by exposure.

The photopolymerization initiator may be selected appropriately from among conventionally used photopolymerization initiators in accordance with the type of photopolymerizable compound used, provided the objects of the present invention are not impaired. Examples of preferred photopolymerization initiators in those cases where a photopolymerizable compound having an ethylenic unsaturated bond is used include 1-hydroxycyclohexyl phenyl ketone, 2-hydroxy-2-methyl-1-phenylpropan-1-one, 1-[4-(2-hydroxyethoxy)phenyl]-2-hydroxy-2-methyl-1-propan-1-one, 1-(4-isopropylphenyl)-2-hydroxy-2-methylpropan-1-one, 1-(4-dodecylphenyl)-2-hydroxy-2-methylpropan-1-one, 2,2-dimethoxy-1,2-diphenylethan-1-one, bis(4-dimethylaminophenyl) ketone, 2-methyl-1-[4-(methylthio)phenyl]-2-morpholinopropan-1-one, 2-benzyl-2-dimethylamino-1-(4-morpholinophenyl)-butan-1-one, 1-[9-ethyl-6-(2-methylbenzoyl)-9H-carbazol-3-yl]ethanone 1-(o-acetyloxime), 2,4,6-trimethylbenzoyldiphenylphosphine oxide, 4-benzoyl-4'-methyldimethylsulfide, 4-dimethylaminobenzoic acid, methyl 4-dimethylaminobenzoate, ethyl 4-dimethylaminobenzoate, butyl 4-dimethylaminobenzoate, 4-dimethylamino-2-ethylhexylbenzoic acid, 4-dimethylamino-2-isoamylbenzoic acid, benzyl-β-methoxyethyl acetal, benzyl dimethyl ketal, 1-phenyl-1,2-propanedione-2-(o-ethoxycarbonyl)oxime, methyl o-benzoylbenzoate, 2,4-diethylthioxanthone, 2-chlorothioxanthone, 2,4-dimethylthioxanthone, 1-chloro-4-propoxythioxanthone, thioxanthene, 2-chlorothioxanthene, 2,4-diethylthioxanthene, 2-methylthioxanthene, 2-isopropylthioxanthene, 2-ethylanthraquinone, octamethylanthraquinone, 1,2-benzanthraquinone, 2,3-diphenylanthraquinone, azobisisobutyronitrile, benzoyl peroxide, cumene peroxide, 2-mercaptobenzimidazole, 2-mercaptobenzoxazole, 2-mercaptobenzothiazole, 2-(o-chlorophenyl)-4,5-di(m-methoxyphenyl)-imidazolyl dimer, benzophenone, 2-chlorobenzophenone, p,p'-bis(dimethylamino)benzophenone, 4,4'-bis(diethylamino)benzophenone, 4,4'-dichlorobenzophenone, 3,3-dimethyl-4-methoxybenzophenone, benzil, benzoin, benzoin methyl ether, benzoin ethyl ether, benzoin isopropyl ether, benzoin n-butyl ether, benzoin isobutyl ether, benzoin butyl ether, acetophenone, 2,2-diethoxyacetophenone, p-dimethylacetophenone, p-dimethylaminopropiophenone, dichloroacetophenone, trichloroacetophenone, p-tert-butylacetophenone, p-dimethylaminoacetophenone, p-tert-butyltrichloroacetophenone, p-tert-butyldichloroacetophenone, α,α-dichloro-4-phenoxyacetophenone, thioxanthone, 2-methylthioxanthone, 2-isopropylthioxanthone, dibenzosuberone, pentyl-4-dimethylamino benzoate, 9-phenylacridine, 1,7-bis-(9-acridinyl)heptane, 1,5-bis-(9-acridinyl)pentane, 1,3-bis-(9-acridinyl)propane, p-methoxytriazine, 2,4,6-tris(trichloromethyl)-s-triazine, 2-methyl-4,6-bis(trichloromethyl)-s-triazine, 2-[2-(5-methylfuran-2-yl)ethenyl]-4,6-bis(trichloromethyl)-s-triazine, 2-[2-(furan-2-yl)ethenyl]-4,6-bis(trichloromethyl)-s-triazine, 2-[2-(4-diethylamino-2-methylphenyl)ethenyl]-4,6-bis(trichloromethyl)-s-triazine, 2-[2-(3,4-dimethoxyphenyl)ethenyl]-4,6-bis(trichloromethyl)-s-triazine, 2-(4-methoxyphenyl)-4,6-bis(trichloromethyl)-s-triazine, 2-(4-ethoxystyryl)-4,6-bis(trichloromethyl)-s-triazine, 2-(4-n-butoxyphenyl)-4,6-bis(trichloromethyl)-s-triazine, 2,4-bis-trichloromethyl-6-(3-bromo-4-methoxy)phenyl-s-triazine, 2,4-bis-trichloromethyl-6-(2-bromo-4-methoxy)phenyl-s-triazine, 2,4-bis-trichloromethyl-6-(3-bromo-4-methoxy)styrylphenyl-s-triazine, and 2,4-bis-trichloromethyl-6-(2-bromo-4-methoxy)styrylphenyl-s-triazine. Among these, from the viewpoint of lowering the cytotoxicity of a chip for cell culture formed using the photosensitive adhesive, a photopolymerization initiator selected from among α-aminoalkylphenone-based photopolymerization initiators and oxime ester-based photopolymerization initiators is preferred. These photopolymerization initiators may be used individually or in combinations containing two or more initiators.

Other Components

In addition to the photopolymerizable compound and the photopolymerization initiator, the photosensitive adhesive may, if required, also include additives such as solvents (for example, propylene glycol-1-methyl ether acetate (PGMEA)), surfactants, adhesion improvers, thermal polymerization inhibitors and defoaming agents. Conventionally known materials can be used for any of these additives. Examples of the surfactants include anionic, cationic and nonionic compounds, examples of the adhesion improvers include conventionally known silane coupling agents, examples of the thermal polymerization inhibitors include hydroquinone and hydroquinone monoethyl ether, and examples of the defoaming agents include silicone-based and fluorine-based compounds.

The thickness of the photosensitive adhesive layer is typically at least 5 µm but not more than 50 µm, and for example is preferably at least 8 µm but not more than 30 µm, or at least 10 µm but not more than 25 µm.

There are no particular limitations on the method used for forming the photosensitive adhesive layer on the first substrate, and examples of methods that may be used include a method of dripping a predetermined amount of the photosensitive adhesive onto the first substrate, methods that use a contact transfer coating device such as a roll coater, reverse coater or bar coater, and methods that use a non-contact coating device such as a spinner (rotary coating device) or a curtain flow coater.

[Step B]

Next, a photosensitive molding material 3' is deposited on the 3D printing substrate 10 produced in the above step A, thus forming a first photosensitive molding material layer 3a. Subsequently, ultraviolet rays 8 are selectively irradiated to selectively cure the first photosensitive molding material layer 3a (see [Step B] of FIG. 1).

(Photosensitive Molding Material)

The photosensitive molding material is used for cell culture, and therefore preferably has low cytotoxicity. Further, the photosensitive molding material is preferably solventless, and preferably has low autofluorescence and low warpability (sometimes also referred to as "low curing shrinkage" or "low elasticity").

Photopolymerizable Compound

The photosensitive molding material can be selected from all manner of photopolymerizable compounds used conventionally as photosensitive molding materials. Examples of these photopolymerizable compounds include the same compounds as those mentioned above in the description of the photopolymerizable compound of the (Photosensitive Adhesive).

Photopolymerization Initiator

The photosensitive molding material contains a photopolymerization initiator in an amount of at least 0.5% by mass but not more than 5.0% by mass, and preferably at least 1.0% by mass but not more than 4.0% by mass, relative to the mass of the photosensitive molding material. By including a photopolymerization initiator in this type of amount in the photosensitive molding material, it is possible to reduce the cytotoxicity caused by residual monomers or photopolymerization initiator within the photosensitive molding material layer obtained upon curing the photosensitive molding material by exposure.

Examples of the photopolymerization initiator include the same compounds as those mentioned above in the description of the photopolymerization initiator of the (Photosensitive Adhesive).

The thickness of the photosensitive molding material layer is, for example, typically at least 0.1 µm but not more than 100 µm, and is preferably at least 1 µm but not more than 80 µm, or at least 1 µm but not more than 60 µm. By ensuring that the thickness of the photosensitive molding material layer falls within this range, the chip for cell culture is able to have high resolution.

Examples of methods that can be used for forming the photosensitive molding material layer on the 3D printing substrate include vat photopolymerization methods (stereolithography methods), and lamination methods using sheets or liquids. In one specific example of a vat photopolymerization method, the 3D printing substrate 10 is placed on an operating table 4 provided inside a tank 5a filled with a liquid photosensitive molding material 3', and ultraviolet rays are irradiated selectively onto the 3D printing substrate 10, thereby achieving selective curing while forming the first photosensitive molding material layer 3a.

In one example of the method for irradiating the ultraviolet rays, ultraviolet rays emitted from a light source such as a high-pressure mercury lamp, ultra-high-pressure mercury lamp, xenon lamp, carbon arc lamp, HeCd laser or Ar laser are passed through a modulator or the like as required and then passed through a lens or the like, and a digital micromirror device or the like is then used to control the irradiation pattern of the rays, while curing is performed until the photosensitive molding material layer reaches a prescribed thickness. The exposure dose of ultraviolet rays irradiated onto the photosensitive molding material layer is determined appropriately with due consideration of the composition of the photosensitive molding material and the thickness of the photosensitive molding material layer. Typically, the exposure dose of ultraviolet rays irradiated onto the photosensitive molding material layer is preferably at least 10 mJ/cm$^2$ but not more than 100,000 mJ/cm$^2$, and is more preferably at least 100 mJ/cm$^2$ but not more than 50,000 mJ/cm$^2$.

FIG. 1 illustrates a method in which the light source is positioned at the top, and lamination is performed while lowering the operating table 4, but a method in which the light source is located underneath, and lamination is performed while raising the operating table 4 may also be used.

[Step C]

Next, further photosensitive molding material 3' is deposited on the selectively cured first photosensitive molding material layer 3a, thereby overlaying a second photosensitive molding material layer 3b, and this overlaid second photosensitive molding material layer 3b is then irradiated selectively with ultraviolet rays, thereby selectively curing the overlaid second photosensitive molding material layer 3b (see [Step C] of FIG. 1).

Specifically, the operating table 4, on which is placed the 3D printing substrate 10 having the selectively cured first photosensitive molding material layer 3a formed thereon, is lowered, and a selective irradiation of ultraviolet rays 8 is performed, thereby achieving selective curing while forming the overlaid second photosensitive molding material layer 3b.

[Step D]

Next, the aforementioned step C is repeated a plurality of times, thereby curing and stacking layers of the photosensitive molding material one layer at a time, and the entire structure is then immersed in a tank 5b containing a developer 9, thereby developing the uncured portions and obtaining a cell culture channel 20a (see [Step D] of FIG. 1).

In [Step D] of FIG. 1, a structure in which two photosensitive molding material layers have been formed is illustrated, but three or more photosensitive molding material layers may also be formed.

In the method for developing the uncured portions, the 3D printing substrate having the overlaid photosensitive molding material layers is immersed in a developer to remove the uncured portions. Examples of the developer include organic solvents such as propylene glycol-1-methyl ether acetate (PGMEA), isopropyl alcohol (IPA) and acetone. Following immersion in the developer, the substrate may be washed with a rinse liquid (such as an organic solvent or water).

Further, following developing, the cell culture channel may be subjected to a plasma treatment. By subjecting the cell culture channel to a plasma treatment, a cell culture channel can be formed to which cells can readily attach. There are no particular limitations on the plasma used for the plasma treatment, and examples include an O$_2$ plasma, N$_2$ plasma or CF$_4$ plasma.

[Step E]

Next, a first adhesive is applied to a second substrate 11 having transparency. By leaving the first adhesive to stand for a certain time to dry, a first adhesive layer 12 is formed, thus obtaining a cell culture channel top plate 20b (see [Step E] of FIG. 1).

(Second Substrate)

From the viewpoint of enabling observation of the cultured cells using a phase contrast microscope or the like, the second substrate preferably has transparency. Further, in order to enhance the transparency, the substrate preferably contains no fillers (antiblocking agents).

Specific examples of materials for the second substrate include the same materials as those mentioned above in the description of the (First Substrate) of [Step A].

The thickness of the second substrate is, for example, at least 50 µm but not more than 250 µm, and is preferably at least 100 µm but not more than 230 µm, or at least 150 µm but not more than 200 µm.

The second substrate may have a slip layer containing a lubricant component on at least one surface.

Examples of the lubricant component include the same components as those mentioned above in the description of the (First Substrate) of [Step A].

There are no particular limitations on the method used for forming the slip layer, and examples include a method in which the slip layer is formed by so-called inline coating, by coating the base substrate material prior to stretching during production of the second substrate, and then performing stretching, and a lamination method that uses coextrusion.

The thickness of the slip layer is, for example, not more than 0.1 µm, and is preferably 50 nm or less.

(First Adhesive)

Because the cells are incubated in a constant-temperature environment at about 37° C., the first adhesive preferably has low deformability in a 37° C. environment. The first adhesive preferably also has adhesiveness to the second substrate, adhesiveness to the cell culture channel formed in the aforementioned steps B to D, good transparency, low autoluminescence, low cytotoxicity, and resistance to sterilizing detergents.

The material for the first adhesive is typically a resin having a Tg value that is preferably at least 5° C., more preferably at least 10° C., and even more preferably 20° C. or higher, and examples include polyester-based resins, acrylic-based resins, urethane-based resins, polyolefin-based resins, fluorine-based resins and silicone-based resins having a Tg value that satisfies the above range, as well as mixtures and modified resins of the above resins. Among the various possibilities, the material for the first adhesive is preferably a polyester-based resin having minimal low-molecular weight residues and therefore low toxicity, and having a Tg value of 5° C. or higher. By using a polyester-based resin having a Tg value of 5° C. or higher as the material for the first adhesive, the adhesive has low deformability in a 37° C. environment, and cells can be cultured stably and safely in a constant-temperature environment of about 37° C.

Specific examples of polyester-based resins having a Tg value of 5° C. or higher include the "Vylon" (a registered trademark) series of resins manufactured by Toyobo Co., Ltd., which are particularly preferred due to the large number of resins that can be obtained.

The polyester-based resin may be crosslinked with a melamine resin or the like. Examples of the melamine resin include the "SUMIMAL" (a registered trademark) series of resins manufactured by Sumitomo Chemical Co., Ltd., and the "CYMEL" (a registered trademark) series of resins manufactured by Mitsui Cytec, Ltd.

From the viewpoint of the balance between workability and the like and durability, the ratio between the resin and the crosslinking agent is preferably set so that the amount of the crosslinking agent (following reaction) in the first adhesive layer following drying is at least 5% by mass but not more than 30% by mass.

The Tg values for the aforementioned Vylon (a registered trademark) series of resins manufactured by Toyobo Co., Ltd. are as follows.

Vylon 103 (47° C.), Vylon 200 (67° C.), Vylon 220 (53° C.), Vylon 226 (65° C.), Vylon 240 (60° C.), Vylon 245 (60° C.), Vylon 270 (67° C.), Vylon 280 (68° C.), Vylon 290 (72° C.), Vylon 296 (71° C.), Vylon 300 (7° C.), Vylon 600 (47° C.), Vylon 630 (7° C.), Vylon 650 (10° C.), Vylon GK110 (50° C.), Vylon GK130 (15° C.), Vylon GK140 (20° C.), Vylon GK150 (20° C.), Vylon GK190 (11° C.), Vylon GK250 (60° C.), Vylon GK330 (16° C.), Vylon GK360 (56° C.), Vylon GK590 (15° C.), Vylon GK640 (79° C.), Vylon GK680 (10° C.), Vylon GK780 (36° C.), Vylon GK810 (46° C.), Vylon GK880 (84° C.), and Vylon GK890 (17° C.). These Tg values are the temperatures recorded on the company's website. Further, the molecular weights (Mn) of these resins are within a range from $3 \times 10^3$ to $30 \times 10^3$.

[Step F]

Next, the cell culture channel 20a obtained in step D and the cell culture channel top plate 20b obtained in step E are positioned against one another and bonded together via the first adhesive layer 12, and the structure is then subjected to thermocompression bonding, thus obtaining a cell culture chip 1A that includes a microchannel structural body having a hollow structure.

In one example of the method used for performing the thermocompression bonding, the structure in a state having the cell culture channel and the cell culture channel top plate bonded together is passed between laminating rollers or the like to perform thermocompression. The temperature during the compression bonding may be set appropriately in accordance with the type of first adhesive used.

Second Embodiment

Because [Step A] to [Step D] are the same as [Step A] to [Step D] described above for the <First Embodiment>, descriptions of those steps are omitted.

After the aforementioned step D, a step H described below may be performed.

[Step H]

Ultraviolet rays are irradiated onto the front surface of the cell culture channel obtained in the aforementioned step D, thereby curing any uncured components (not shown in the drawings). This enables any uncured photopolymerizable compounds contained in the photosensitive molding material layers and the photosensitive adhesive layer to be adequately cured.

Examples of the method used for irradiating the ultraviolet rays include the same methods as those described above in relation to [Step B]. The exposure dose of ultraviolet rays irradiated onto the cell culture channel is preferably at least 10 mJ/cm² but not more than 200,000 mJ/cm², and is more preferably at least 100 mJ/cm² but not more than 100,000 mJ/cm².

Step E and step F that are performed after step H are the same as [Step E] and [Step F] described above in relation to the <First Embodiment>, and therefore descriptions of these steps are omitted.

Third Embodiment

Because [Step A] to [Step H] are the same as [Step A] to [Step H] described above for the <First Embodiment> and the <Second Embodiment>, descriptions of those steps are omitted.

After the aforementioned step H, a step I described below may be performed.

[Step I]

The cell culture channel that has been cured by irradiation of ultraviolet rays onto the front surface is washed using an organic solvent, thereby removing any uncured components (not shown in the drawings). This enables any uncured photopolymerizable compounds remaining in the cell culture channel to be adequately removed.

Examples of organic solvents that can be used include non-polar solvents such as hexane, benzene, toluene, diethyl ether, chloroform, ethyl acetate, methylene chloride, PGMEA and propylene glycol monomethyl ether; and polar solvents such as tetrahydrofuran, acetone, acetonitrile, N,N-dimethylformamide, dimethyl sulfoxide, acetic acid, 1-butanol, 1-propanol, 2-propanol, ethanol, methanol, formic acid and water, although this is not an exhaustive list. These solvents may be used individually, or a combination of two or more solvents may be used.

The method used for performing washing with the organic solvent preferably involves first performing washing with a non-polar solvent, and then gradually changing to washing with a polar solvent. In one specific method, the cell culture channel is washed with PGMEA, propylene glycol monomethyl ether, and then ethanol, in that order, and is then dried.

Step E and step F that are performed after step I are the same as [Step E] and [Step F] described above in relation to the <First Embodiment>, and therefore descriptions of these steps are omitted.

Further, the chip for cell culture of the present embodiment may also have a support, provided beneath the chip with a second adhesive layer disposed therebetween, in order to ensure a high degree of strength.

(Support)

From the viewpoint of enabling observation of the cultured cells using a phase contrast microscope or the like, the support preferably has transparency.

Examples of the material for the support include glass, polyethylene terephthalates, polycarbonates, cycloolefin polymers, polydimethylsiloxanes, polystyrenes and polyacrylates, but there are no particular limitations on the material.

(Second Adhesive)

From the viewpoint of enabling observation of the cultured cells using a phase contrast microscope or the like, the second adhesive preferably has transparency. Further, the second adhesive preferably exhibits adhesiveness to the support and the first substrate.

Examples of the second adhesive include the same adhesives as those mentioned above in the description of the (First Adhesive).

EXAMPLES

The present invention is described below in further detail using a series of examples and comparative examples, but the present invention is in no way limited to these examples.

[Production Example 1] Production of Cell Culture Chip 1

1. Preparation of 3D Printing Substrate
(1) Preparation of First Photosensitive Adhesive The raw materials shown below in Table 1 were stirred together thoroughly to form a uniform solution, thus obtaining a first photosensitive adhesive.

TABLE 1

| Raw material name | Parts by mass |
| --- | --- |
| ARONIX M313 (manufactured by Toagosei Co., Ltd.) | 100 |
| Irgacure 184 (manufactured by BASF Corporation) | 3 |
| Propylene glycol monomethyl ether acetate (PGMEA) | 100 |

(2) Preparation of 3D Printing Substrate

Subsequently, the first photosensitive adhesive obtained in (1) was applied, in an amount sufficient to form a dried film thickness of 15 μm, to the surface of a slip layer 102 (treated surface for facilitating bonding) of a COSMOSHINE A4100 film with a film thickness of 188 μm (a polyethylene terephthalate substrate 101, manufactured by Toyobo Co., Ltd.) (the first substrate), thus obtaining a 3D printing substrate 100 (see FIG. 2).

2. Preparation of Cell Culture Channel
(1) Preparation of Photosensitive Molding Material The raw materials shown below in Table 2 were stirred together thoroughly to form a uniform solution, thus obtaining a photosensitive molding material.

TABLE 2

| Raw material name | Parts by mass |
| --- | --- |
| Viscoat #360 (manufactured by Osaka Organic Chemical Industry Ltd.) | 50 |
| EBECRYL 8802 (manufactured by Daicel Allnex Ltd.) | 50 |
| KAYACURE DETX-S (manufactured by Nippon Kayaku Co., Ltd.) | 3 |
| KAYACURE EPA (manufactured by Nippon Kayaku Co., Ltd.) | 3 |

(2) Preparation of Cell Culture Channel

Subsequently, the photosensitive molding material obtained in (1) was coated onto the 3D printing substrate 100 in an amount sufficient to form a single layer thickness of 20 to 50 μm, and a digital micromirror device (DMD) was then used to selectively irradiate ultraviolet rays with a central wavelength of 370 μm to cure the photosensitive molding material.

The same method was then used to form and cure multiple layers of the photosensitive molding material, and the resulting structure was developed for three minutes in acetone and then dried by air blowing to obtain a structural body having a microchannel subsequently, a high-pressure mercury lamp was used to irradiate ultraviolet rays onto the entire structure, washing was then performed sequentially with PGMEA, propylene glycol monomethyl ether and then ethanol, and the structure was dried to obtain a cell culture channel 200a (see FIG. 2).

3. Preparation of Cell Culture Channel Top Plate
(1) Preparation of First Adhesive The raw materials shown below in Table 3 were stirred together thoroughly to form a uniform solution, thus obtaining a first adhesive.

TABLE 3

| Raw material name | Parts by mass |
| --- | --- |
| Vylon GK780 (manufactured by Toyobo Co., Ltd.) (Tg: 36° C.) | 20 |
| Cyclohexanone | 100 |

(2) Preparation of Cell Culture Channel Top Plate

Subsequently, the first adhesive obtained in (1) was applied, in an amount sufficient to form a dried film thickness of 20 μm, to the untreated surface of a COSMOSHINE A4100 film with a film thickness of 188 μm (a polyethylene terephthalate substrate 106, manufactured by Toyobo Co., Ltd.) (the second substrate), a carbon dioxide gas laser was then used to open inlet holes (labeled as a1 (3 mm) and c1 (1.5 mm) in FIG. 2) in the film, and the structure was then immersed in ethanol and then dried to obtain a cell culture channel top plate 200b (see FIG. 2).

4. Preparation of Cell Culture Chip (Affixing of Cell Culture Channel Top Plate to Cell Culture Channel)

Figure 2:
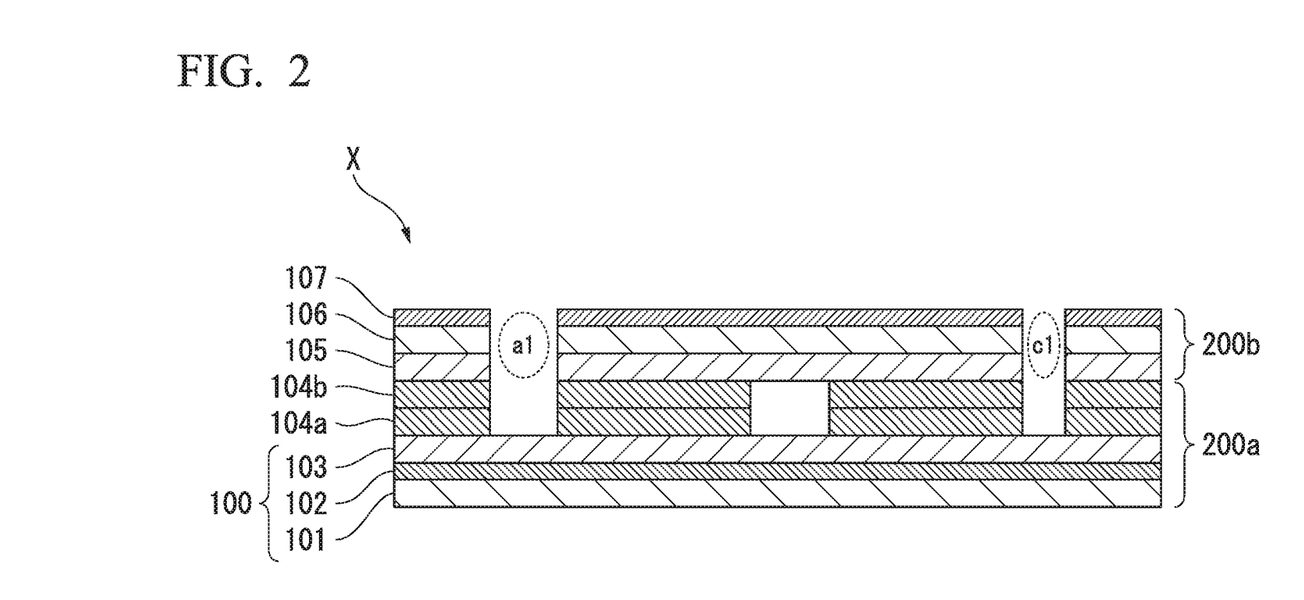
FIG. 2 is a cross-sectional view schematically illustrating the structure of a microchannel chip for cell assay in Production Example 1 of the present invention.

Next, a double-sided tape with a thickness of 50 μm was affixed to the cell culture channel top plate 200b as a temporary holding agent, a microscope was used to position the cell culture channel top plate 200b so that the holes (a1 (3 mm) and c1 (1.5 mm) in FIG. 2) could be affixed to prescribed locations on the cell culture channel 200a, and the surface of the cell culture channel top plate 200b coated with the first adhesive and the cell culture channel 200a were temporarily affixed together. Subsequently, thermocompression bonding was performed by passing the structure between laminating rollers that had been heated to 80° C., thus obtaining a cell culture chip 1 (X) having a hollow structure (see FIG. 2).

[Production Example 2] Production of Cell Culture Chip 2

With the exception of replacing the first adhesive mentioned in "3. Preparation of Cell Culture Channel Top Plate" of the above Production Example 1, and instead using a second adhesive, a cell culture chip 2 was produced using the same methods as those described in Production Example 1. The second adhesive was obtained by thoroughly stirring the raw materials shown below in Table 4 to form a uniform solution.

TABLE 4

| Raw material name | Parts by mass |
| --- | --- |
| Elitel UE3220 (manufactured by Unitika Ltd.) (Tg: 5° C.) | 20 |
| Cyclohexanone | 80 |

[Production Example 3] Production of Cell Culture Chip 3

With the exception of replacing the first adhesive mentioned in "3. Preparation of Cell Culture Channel Top Plate" of the above Production Example 1, and instead using a third adhesive, a cell culture chip 3 was produced using the same methods as those described in Production Example 1. The third adhesive was obtained by thoroughly stirring the raw materials shown below in Table 5 to form a uniform solution.

TABLE 5

| Raw material name | Parts by mass |
| --- | --- |
| Vylon 550 (manufactured by Toyobo Co., Ltd.) (Tg: −15° C.) | 20 |
| Cyclohexanone | 80 |

[Test Example 1] Cell Culture Test Using Cell Culture Chip 1

1. Bonding of Cell Culture Chip 1 and Culture Solution Storage Tank

First, in order to enable cell culturing to be performed using the cell culture chip, a culture solution storage tank was formed from a silicone resin (SILPOT 184 W/C, manufactured by Dow Corning Toray Co., Ltd.). Specifically, a silicone resin prepolymer was injected into a mold prepared by machining PEEK, and following vacuum degassing, the resin was heated at 70 to 80° C. for 2 hours to prepare the culture solution storage tank.

Subsequently, an adhesive (Cemedine Super X, manufactured by Cemedine Co., Ltd.) was used to bond the culture solution storage tank to positions at the inlet holes (a1 and c1) of the cell culture channel of the cell culture chip 1 produced in Production Example 1, and the structure was then heated at 70 to 80° C. for 2 hours. Subsequently, the cell culture chip 1 was sterilized by irradiation with ultraviolet rays for about 20 minutes. Using the cell culture chip 1 with the bonded culture solution storage tank, a cell culture test was then performed in accordance with the method described below.

2. Method for Vacuum Treatment of Cell Culture Channel

A phosphate buffer solution (manufactured by Sigma-Aldrich Corporation, Dulbecco's phosphate buffered saline) was placed in the culture solution storage tank, the entire chip was placed inside a vacuum chamber, and a diaphragm pump (DIVAC 0.6 L, manufactured by DIVAC GmbH) was used to perform evacuation at room temperature for one hour, thereby filling the cell culture channel with the phosphate buffer solution.

3. Coating of Cell Culture Channel

Subsequently, the phosphate buffer solution inside the culture solution storage tank was removed by suction, and about 200 μL of a 0.2 mg/mL fibronectin solution (Fibronectin, manufactured by Sigma-Aldrich Corporation) was added to the culture solution storage tank. Next, the culture solution storage tank was pressurized at a pressure of 20 kPa for 4 minutes, thereby introducing the fibronectin solution into the cell culture channel. Pressure adjustment was performed using an air pump (Mini Air Pump EAP-01, manufactured by As One Corporation) and a regulator (High-Performance Pressure Regulator PR-4000, manufactured by GL Sciences Inc.), and the pressure was measured using a pressure meter (Handy Manometer PG-100 102GP, manufactured by Copal Electronics Corporation). The structure was then left to stand at room temperature for one hour, thus coating the cell culture channel with fibronectin. Subsequently, the fibronectin solution remaining inside the culture solution storage tank was removed by suction. Next, about 200 μL of a culture solution (Dulbecco's Modified Eagle Medium, manufactured by Gibco Inc.) containing 5% blood serum (HyClone Fetal Bovine Serum, manufactured by Thermo Fisher Scientific Inc.) and 1% of an antibiotic (Penicillin-Streptomycin Solution, manufactured by Nacalai Tesque, Inc.) was introduced into the culture solution storage tank, and the culture solution storage tank was pressurized at a pressure of 20 kPa for 4 minutes to replace the solution in the cell culture channel with the culture solution.

4. Cell Introduction and Static Culture

NIH3T3 cells available from Riken were cultured in the culture solution and collected using a 0.25% trypsin-EDTA solution (manufactured by Thermo Fisher Scientific Inc.). The collected cells were suspended in the culture solution at a concentration of $5\times10^5$ cells/mL. Next, about 200 μL of the cell suspension was added to the culture solution storage tank, and the culture solution storage tank was pressurized at a pressure of 20 kPa for 4 minutes to introduce the cell suspension into the cell culture channel, with microscope observation being used to confirm that the cells had been introduced into the cell culture channel. The cell suspension remaining in the culture solution storage tank was removed by suction, the culture solution was added to the culture solution storage tank, and the structure was left to stand at 37° C. in air containing 5% of carbon dioxide under conditions of saturated water vapor pressure to promote adhesion of the cells.

5. Perfusion Culture

After static culturing for about 6 hours, once confirmation had been made that the cells had adhered to the cell culture channel, 500 μL of the culture solution was added to the culture solution storage tank. Perfusion culture was then performed by subjecting the culture solution storage tank containing the culture solution to repeated intermittent pressurization involving 4 minutes pressurization at 5 kPa and then 176 minutes of atmospheric pressure release. The culture solution inside the culture solution storage tank was replaced with fresh culture solution once per day. At this time, the culture medium flow rate during the perfusion culture was measured by measuring the weight of culture solution remaining in the culture solution storage tank. The perfusion culture was continued until the third day following introduction of the cells. Further, during culturing, the state of the cells was observed using an inverted fluorescence microscope (IX71, manufactured by Olympus Corporation), and a phase contrast microscope image was acquired.

6. Live/Dead Staining

After 3 days of perfusion culture, in order to confirm the live/dead ratio of the cells in the cell culture channel, a Live/Dead staining reagent (LIVE/DEAD (a registered trademark) Viability/Cytotoxicity Kit, for mammalian cells, manufactured by Life Technologies Corporation) was used to stain the cells inside the cell culture channel. The Live/Dead staining was performed in accordance with the following protocol. First, a Live/Dead staining solution was prepared by adding and mixing 4 μL of the Calcein AM solution and 16 μL of the Ethidium homodimer-1 solution included in the Live/Dead staining reagent with 4 mL of a phosphate buffer solution. Next, about 200 μL of the phosphate buffer solution was introduced into the culture solution storage tank, and the inside of the cell culture channel was washed by pressurizing the culture solution storage tank at 20 kPa for 4 minutes. Subsequently, about 200 μL of the Live/Dead staining solution was added to the culture solution storage tank, this Live/Dead staining solution was then introduced into the cell culture channel by pressurizing the culture solution storage tank at 20 kPa for 4 minutes, and staining was then performed in the dark at room temperature for about 30 minutes. Subsequently, the inverted fluorescence microscope (IX71, manufactured by Olympus Corporation) was used to acquire a fluorescence microscope image. The fluorescence image was acquired using a fluorescence filter (Multiband Filter (ET-DAPI/FITC/Texas Red) manufactured by Chroma ATE Inc.) that conformed to FITC (green fluorescence: fluorescence wavelength 488 nm, excitation wavelength 530 nm) and Texas Red (red fluorescence: fluorescence wavelength 590 nm, excitation wavelength 615 nm).

7. Results

When NIH3T3 cells were cultured and then observed using a phase contrast microscope in accordance with the method described above, the cells were observed to have adhered and were spreading one day after cell introduction, and the cells were also seen to proliferate throughout the 3 days of perfusion culture. Two additional cell culture chips 1 of the same type were produced and tested in the same manner, and the cell culturing was confirmed with good reproducibility, with minimal differences in the adhesion, spreading and proliferation of the cells.

Further, the flow rate of the culture solution was stable during the 3 days of perfusion culture at 37° C. In order to confirm the reproducibility of the culture solution flow rate, two cell culture chips 1 each having four cell culture channels were produced, and the flow rate of the culture solution in each of the total of 8 cell culture channels was measured each day for 3 days. The measured values for the flow rates of the 8 cell culture channels across the 3 days satisfied 274±26 µL/day (mean value±standard deviation), confirming that the variation in flow rate for each cell culture channel was small, and the flow rate was also stable over time.

Furthermore, in the Live/Dead staining performed following the perfusion culturing, almost all (at least 95%) of the cells inside the cell culture channel were confirmed as being live cells stained by the Calcein, confirming that culturing was able to be performed with a high survival rate. Further, a small number (not more than 5%) of the cells were confirmed as being dead cells stained by the Ethidium homodimer-1.

These results confirmed that when cells inside the cell culture channel of the cell culture chip 1 produced in Production Example 1 were stained, observation was possible using both green fluorescence and red fluorescence.

The above test confirmed that the cell culture chip 1 produced in Production Example 1 could be used to perform cell culturing by perfusion of the culture solution at 37° C., and that the cells proliferated during perfusion culture, with the proliferated cells maintaining a high survival rate. Further, the test also confirmed that, by using the cell culture chip 1 produced in Production Example 1, the flow rate of the culture solution during the perfusion culture was stable, and bright field observation and fluorescence observation (green fluorescence and red fluorescence) of the cells were possible.

[Test Example 2] Cell Culture Test Using Cell Culture Chip 2

With the exception of using the cell culture chip 2 produced in Production Example 2, the same method as that described in Production Example 1 was used to bond a culture solution storage tank, and the cell culture chip 2 with the bonded culture solution storage tank was then used to perform a cell culture test using the same method as that described for Test Example 1.

The results of performing a test in the same manner as Test Example 1 confirmed that, with the cell culture chip 2 produced in Production Example 2, the flow rate of the culture solution during the perfusion culture was stable, and bright field observation and fluorescence observation (green fluorescence and red fluorescence) of the cells were possible.

[Test Example 3] Cell Culture Test Using Cell Culture Chip 3

With the exception of using the cell culture chip 3 produced in Production Example 3, the same method as that described in Production Example 1 was used to bond a culture solution storage tank, and the cell culture chip 3 with the bonded culture solution storage tank was then used to perform a cell culture test using the same method as that described for Test Example 1.

The results of performing a test in the same manner as Test Example 1 revealed that, with the cell culture chip 3 produced in Production Example 3, the third adhesive applied to the cell culture channel top plate deformed during the static culture performed at 37° C. for 6 hours, and the channel became totally blocked. An attempt was made to perfuse the culture solution by introducing the medium into the culture solution storage tank and pressurizing the tank, but because the channel was blocked, perfusion of the culture solution was impossible. Subsequently, pressurization to enable perfusion of the culture solution was continued for 2 days under continuous observation, but because the channel was blocked, perfusion of the culture solution was not possible, and the state of the cells that had been introduced into the cell culture channel was seen to deteriorate. Furthermore, because of the channel blockage, Live/Dead staining could not be performed.

The above test confirmed that, with the cell culture chip 3 produced in Production Example 3, cell culturing by perfusion of the culture solution at 37° C. was impossible.

INDUSTRIAL APPLICABILITY

The present invention enables mass production at low cost of a chip for cell culture having a microchannel structure.

DESCRIPTION OF THE REFERENCE SIGNS

1A: Cell culture chip
1: First substrate
2: Photosensitive adhesive layer
3a: First photosensitive molding material layer
3b: Second photosensitive molding material layer
3': Liquid photosensitive molding material
4: Operating table
5a: First tank
5b: Second tank
6: Laser irradiation device
7: Mirror
8: Ultraviolet rays
9: Developer
10: 3D printing substrate
11: Second substrate
12: First adhesive layer
20a: Cell culture channel
20b: Cell culture channel top plate
100: 3D printing substrate
101: PET substrate (first substrate)
102, 107: Slip layer
103: First photosensitive adhesive layer
104a: First photosensitive molding material layer
104b: Second photosensitive molding material layer
105: First adhesive layer
106: PET substrate (second substrate)
200a: Cell culture channel
200b: Cell culture channel top plate
X: Cell culture chip 1

The invention claimed is:
1. A method for producing a chip for cell culture, the method comprising:
a step A of forming a photosensitive adhesive layer by applying a photosensitive adhesive to a first substrate having transparency, thus obtaining a 3D printing substrate, a step B of depositing a photosensitive molding material on the 3D printing substrate to form a photosensitive molding material layer, and then selectively irradiating the photosensitive molding material layer with ultraviolet rays to selectively cure the photosensitive molding material layer, a step C of overlaying another photosensitive molding material layer by depositing a photosensitive molding material on the selectively cured photosensitive molding material layer, and then selectively irradiating the overlaid photosensitive molding material layer with ultraviolet rays to selectively cure the overlaid photosensitive molding material layer, a step D of repeating the step C a plurality of times, and subsequently developing uncured portions to obtain a cell culture channel, a step E of forming a first adhesive layer by depositing a first adhesive on a second substrate having transparency, thus obtaining a cell culture channel top plate, and a step F of bonding the cell culture channel and the cell culture channel top plate together via the first adhesive layer, and then performing thermocompression bonding to obtain a microchannel structural body having a hollow structure, wherein the first adhesive is a polyester-based resin having a Tg value of 5° C. or higher, and a molecular weight (Mn) of $3 \times 10^3$ to $30 \times 10^3$.

2. The method for producing a chip for cell culture according to claim 1, further comprising, after the step D, a step H of irradiating ultraviolet rays onto a front surface of the cell culture channel to cure uncured components.

3. The method for producing a chip for cell culture according to claim 2, further comprising, after the step H, a step I of washing the cell culture channel using an organic solvent to remove uncured components.

4. The method for producing a chip for cell culture according to claim 3, wherein in the step I, the cell culture channel is washed while gradually changing the solvent from a non-polar solvent to a polar solvent.

* * * * *